United States Patent [19]

Chambers et al.

[11] Patent Number: 4,554,267
[45] Date of Patent: Nov. 19, 1985

[54] CATALYST AND METHOD FOR ORTHO-ALKYLATION OF HYDROXYAROMATIC COMPOUNDS

[75] Inventors: Gregory R. Chambers, Rexford; James G. Bennett, Jr., Glenmont, both of N.Y.

[73] Assignee: General Electric Company, Schenectady, N.Y.

[21] Appl. No.: 500,684

[22] Filed: Jun. 3, 1983

[51] Int. Cl.[4] .......................... B01J 23/76; C07C 37/16
[52] U.S. Cl. ..................................... 502/340; 502/344; 502/345; 568/794; 568/804
[58] Field of Search ....................... 568/780, 794, 804; 502/340, 344, 345

[56]         References Cited
        U.S. PATENT DOCUMENTS

| 1,500,794 | 7/1924 | Bouvier et al. | 502/340 |
| 1,913,774 | 6/1933 | Seib | 502/340 |
| 2,524,566 | 10/1950 | Houtman et al. | 502/340 |
| 3,304,268 | 2/1967 | Lester et al. | 502/340 |
| 3,446,856 | 5/1969 | Hamilton | 260/620 |
| 4,165,539 | 8/1979 | Smith | 568/804 |
| 4,201,880 | 5/1980 | van Sorge | 568/804 |

FOREIGN PATENT DOCUMENTS

| 6927367 | 3/1967 | Japan | 568/804 |
| 0040430 | 3/1982 | Japan | 502/340 |
| 0070839 | 4/1983 | Japan | 502/340 |
| 0079839 | 4/1983 | Japan | 502/340 |
| 0697179 | 11/1979 | U.S.S.R. | 502/340 |

Primary Examiner—Werren B. Lone
Attorney, Agent, or Firm—William H. Pittman; James C. Davis, Jr.; James Magee, Jr.

[57]            ABSTRACT

Hydroxyaromatic compounds such as phenol are alkylated with alkanols such as methanol in the presence of a catalyst comprising magnesium oxide with up to about 0.1% by weight of copper deposited thereon in a layer of submicroscopic thickness. The catalyst is prepared by preparing a slurry of a substantially water-insoluble magnesium reagent such as magnesium hydroxide or magnesium carbonate in an aqueous solution of at least one copper salt, removing and drying the solid phase, and calcining the same at a temperature within the range of about 350°–550° C. The catalyst promotes ortho-alkylation of the hydroxyaromatic compound in high yield, minimizes decomposition of the alkanol, and has long life.

29 Claims, No Drawings

CATALYST AND METHOD FOR ORTHO-ALKYLATION OF HYDROXYAROMATIC COMPOUNDS

This invention relates to new catalyst compositions and methods for their preparation and use, and more particularly to catalysts having improved selectivity for ortho-alkylation of hydroxyaromatic compounds with alkanols and resulting in decreased by-product formation during said alkylation.

Ortho-alkylated hydroxyaromatic compounds are known to be useful for various purposes. For example, 2-alkyl- and 2,6-dialkylphenols may be oxidatively coupled to yield polyphenylene oxides, some of which are used as constituents of engineering plastics.

A typical method for preparation of such compounds is by alkylation of the precursor hydroxyaromatic compound with a primary or secondary alkanol in the presence of a suitable catalyst. The use of magnesium oxide catalysts for this purpose is disclosed in U.S. Pat. Nos. 3,446,856 and 4,201,880. According to Japanese Kokai No. 69/27367, the selectivity of such catalysts for o-alkylation is improved by combining them with 0.5-50% by weight of copper or a similar metal.

Notwithstanding the above-identified disclosures, various problems still exist with the alkylation methods and the catalysts used therein. In the first place, the active life of many of these catalysts is undesirably short, sometimes less than 50 hours.

In the second place, many of such methods and catalysts still produce an undesirably high proportion of p-alkylated products of marginal utility. Thus, alkylation of phenol with methanol in the presence of magnesium oxide yields o-cresol and 2,6-xylenol, the desired products, but in addition yields substantial amounts of such p-substituted compounds as p-cresol, 2,4-xylenol and mesitol (2,4,6-trimethylphenol). These p-substituted compounds are much less useful than the corresponding compounds containing unsubstituted para positions, since they do not yield polymers with the desirable properties possessed by the polyphenylene oxides prepared from such compounds as 2,6-xylenol.

In the third place, the high temperatures (above 460° C. and frequently above 500° C.) required for alkylation using previously known catalysts require an undesirably high energy input and decrease catalyst life. In addition, such temperatures introduce other problems such as thermal decomposition of the reactants. For example, methanol is dehydrogenated under alkylation conditions to formaldehyde, a desirable reaction since the aldehyde is a necessary alkylation intermediate. However, at extremely high temperatures a substantial amount of formaldehyde decomposes to carbon monoxide and hydrogen. Such decomposition products are of little use except as fuel. It is strongly preferred to minimize decomposition of methanol and formaldehyde so as to enable their use for alkylation.

A principal object of the present invention, therefore, is to produce novel catalysts useful for alkylation of hydroxyaromatic compounds.

A further object is to produce catalysts with long life and a high degree of selectivity for ortho-alkylation.

A further object is to provide catalysts which minimize loss of alkanol and high energy usage in the alkylation process.

A further object is to provide an improved process for the ortho-alkylation of hydroxyaromatic compounds with alkanols.

A still further object is to optimize alkanol usage during said alkylation.

Other objects will in part be obvious and will in part appear hereinafter.

The above objects are attained according to the present invention by providing a method for preparing a solid catalyst composition which comprises preparing, at a temperature within the range of about 50°-100° C., a slurry of (1) a substantially water-insoluble magnesium reagent which yields magnesium oxide upon calcination in (2) an aqueous solution of at least one copper salt, the copper content of said slurry being up to about 0.1% by weight of the magnesium reagent content thereof, thereby producing a magnesium-containing solid phase with a copper-containing coating of submicroscopic thickness thereon; removing and drying said solid phase; and calcining the same at a temperature within the range of about 350°-550° C.

Any substantially water-insoluble magnesium reagent which yields magnesium oxide upon calcination may be used in the catalyst preparation method of this invention. The preferred reagents are magnesium oxide, magnesium hydroxide, magnesium carbonate and mixtures thereof. Magnesium oxide exists in an inactive "dead burned" and a "reactive" form; the latter is converted to magnesium hydroxide upon contact with water, and therefore it may be used according to this invention. Particularly useful as a magnesium reagent is basic magnesium carbonate, which is a commercially available material. It is also known as magnesium carbonate hydroxide and is identified in *The Merck Index,* Ninth Edition, in monograph #5483 as having the approximate formula $(MgCO_3)_4 \cdot Mg(OH)_2 \cdot 5H_2O$.

The copper salt may be either cuprous or cupric; cupric salts are generally preferred because of their ready availability. Illustrative copper salts are cuprous chloride, cupric acetate, cupric bromide, cupric chloride, cupric nitrate and cupric sulfate. Also included are coordination complexes of copper, exemplified by the complexes with ammonia and amines. The copper salt should have some solubility in water, but it need not be soluble in high proportions since a relatively small amount of it is used.

According to this invention, an aqueous slurry containing the copper salt and magnesium reagent is prepared, typically by gradual addition of an aqueous solution of the copper salt to a slurry of the magnesium reagent in water at a temperature of about 50°-100° C., preferably about 70°-80° C. The slurry thus obtained typically contains about 10-35% and preferably about 10-15% by weight of the magnesium reagent. The copper content thereof is up to about 0.1% and usually about 0.02-0.04% of the weight of the magnesium reagent.

The aqueous slurry prepared may be agitated, typically with heating within the same range, after addition of the copper salt. During this process the copper salt is deposited on the surface of the magnesium reagent in a layer of submicroscopic thickness. Preferably, the copper distribution on the magnesium reagent is relatively uniform; it has been found that the activity of the catalyst in the alkylation reaction decreases with a decrease in uniformity of the copper layer.

Following deposition of the copper on the magnesium reagent, the solid phase is separated, usually by filtration or centrifugation, and dried, usually by heating at a temperature up to about 200° C., typically in a vacuum oven. For the sake of convenience of storage and use, it is frequently preferred to pelletize the solid phase after drying and before calcining. This is ordinarily effected by sieving (typically through a 25 mesh sieve), milling and compressing. To facilitate pelletizing, binders, fillers and/or pelletizing lubricants known in the art (hereinafter collectively designated "fillers") may be incorporated into the catalyst. Typical of these are graphite and polyphenylene oxide. The filler content of the pelletized solid may be up to about 25% by weight based on copper plus magnesium oxide, depending on the filler used; polyphenylene oxide is most often used in an amount up to about 20%, and graphite in an amount up to about 5%.

The solids are then calcined by heating at a temperature within the range of about 350°–550° C. During calcination, the magnesium reagent is converted to magnesium oxide which is the active magnesium species in the catalyst. Calcination temperatures higher than about 550° C. are undesirable since they may result in sintering of the magnesium oxide, with a decrease in surface area and consequently in catalyst activity.

The active copper species in the alkylation catalyst is believed to be elemental copper. Therefore, it is important to reduce combined copper in the solids to the elemental state. Reduction may be effected before, during or after calcination, and the conditions of calcination determined accordingly. Thus the calcination atmosphere may be oxidizing (e.g., oxygen or air), inert (e.g., nitrogen) or reducing (e.g., hydrogen or other reducing agents). The presence of substances such as water, alkanol and hydroxyaromatic compound is also permissible.

Calcination in a reducing atmosphere is frequently preferred. For example, it may be effected in the presence of hydrogen, typically at about 375°–550° C. It is often most preferred to calcine at about 350°–450° C., preferably about 360°–380° C., in contact with the alkanol-hydroxyaromatic compound feed stream for alkylation. The copper is then reduced by alkanol which is oxidized to the corresponding aldehyde, the essential alkylation intermediate.

In general, the solid catalyst compositions produced by the method of this invention comprise magnesium oxide and up to about 0.1% by weight, based on said magnesium oxide, of copper, said copper being deposited on said magnesium oxide in elemetal or chemically combined form in a layer of submicroscopic thickness. It is believed that the copper layer is essentially monoatomic. Catalyst compositions of this type are also an aspect of the invention. The copper content therein, based on magnesium oxide, is generally about the same as the copper content of about 0.02–0.04%. In terms of surface area, the preferred range of the catalyst composition is about 50–400 and most often about 100–250 m.²/g.

The preparation of the catalyst compositions of this invention is illustrated by the following examples.

EXAMPLE 1

Basic magnesium carbonate, 400 grams, was added at 80° C., with stirring, to 2500 ml. of distilled water. The resulting slurry was stirred for 30 minutes at 80° C., after which a solution of 0.38 gram of cupric nitrate trihydrate in 200 ml. of water was added at the same temperature over one hour, with stirring. Heating and stirring were continued for two hours, after which time substantially no copper was left in the liquid phase. The mixture was filtered and the solids were dried in vacuum at 120° C. for 16 hours.

The dry solids were broken up and put through a 25 mesh sieve. There was added 2 grams (0.5% by weight) of graphite and the mixture was milled in a jar mill, precompressed, reground to 25 mesh and pelletized in cylindrical pellets, 3/16 inch in diameter and ⅛ inch long. The tablets were calcined in an alkylation reactor during use by heating from 370° C. to 440° C. in the presence of a phenol-methanol feed (as described in Example 6) to yield the desired catalyst composition which contained 0.025% copper by weight based on magnesium oxide.

EXAMPLES 2–3

Following the procedure of Example 1, catalysts containing 0.05% and 0.1% copper, respectively, were prepared.

EXAMPLE 4

A catalyst was prepared by the procedure of Example 1 except that 8 grams (2% by weight) of polyphenylene oxide was added with the graphite prior to pelletizing.

EXAMPLE 5

A catalyst was prepared by the procedure of Example 1 except that 10% by weight polyphenylene oxide was incorporated therein and calcination and reduction were effected by heating at 500° C. in a hydrogen atmosphere for 4 hours.

The hydroxyaromatic compounds which may be alkylated with the catalyst of this invention include all of such compounds which have a free ortho-position. As disclosed in the aforementioned U.S. Pat. Nos. 3,446,856 and 4,201,880, the disclosures of which are incorporated by reference herein, suitable hydroxyaromatic compounds include those having the formula

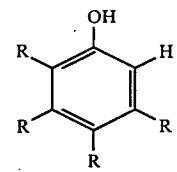

wherein each R is hydrogen, lower alkyl, phenyl or lower alkyl-substituted phenyl. Examples of compounds which may be alkylated are phenol, 1-naphthol, 2-naphthol, o-cresol, m-cresol, p-cresol, 2,4-xylenol, o-ethylphenol, p-isopropylphenol, p-n-butylphenol, 2,4-diethylphenol, catechol, resorcinol and hydroquinone. In general, any alkyl substituents will be primary or secondary, preferably primary, and will contain up to about 4 carbon atoms. The most preferred hydroxyaromatic compounds are the monohydroxyaromatic compounds and especially those in which the para-position is unsubstituted. Phenol, i.e., monohydroxybenzene, is the preferred hydroxyaromatic compound. o-Cresol, which is a by-product in the methylation of phenol to 2,6-xylenol, is somewhat less preferred. Mixtures of any of these compounds may also be used.

The alkanol used for alkylation may be primary or secondary and is usually primary. It is most often a lower alkanol, that is, one containing up to 7 carbon atoms. Illustrative alkanols are methanol, ethanol, 1- propanol, 2-propanol, 1-butanol, 2-methyl-1-propanol and 1-hexanol. Expecially preferred are alkanols containing up to 4 carbon atoms. For reasons of availability, cost and particular utility of the alkylated product, methanol is the most preferred alkanol.

Except when otherwise noted herein, the alkylation conditions used according to this invention are those described in the aforementioned U.S. Pat. Nos. 3,446,856 and 4,201,880. Pressures may vary from atmospheric to as high as about 150 psig. but usually need be no higher than about 30 psig. The proportion of catalyst with respect to reactants is conveniently defined in terms of liquid hourly space velocity (LHSV), which is the volume of liquid feed per unit volume of catalyst per hour, and is typically about 0.5–5.0 and preferably about 1.5–2.5.

The maximum alkylation temperature employed according to this invention is about 475° C. A typical alkylation temperature range is about 400°–475° C. and preferably about 420°–450° C. For the most part, the temperatures within this range are substantially lower than those disclosed in the aforementioned patents. In addition to decreasing the necessary energy input, the use of these lower temperatures minimizes alkanol wastage.

The utility of the catalysts of this invention in the alkylation of hydroxyaromatic compounds is illustrated by the following examples. All percentages are by weight.

EXAMPLE 6

A reactor was loaded with 110 ml. of the catalysts of Examples 1–3, respectively, and heated to 370° C. The reactor was pressurized with nitrogen to 25 psig. and nitrogen was passed through as the temperature was increased to a maximum of 440° C. After 15 minutes, a mixture of 128 grams of methanol, 94 grams of phenol and 44 grams of water (4:1 molar ratio of methanol to phenol) was fed to the reactor at 215 ml./hr. (LHSV of 2.0). The alkylation was run for 502 hours, during which the yields of o-cresol, 2,6-xylenol, p-cresol, 2,4-xylenol and mesitol were monitored and weighted averages calculated. The selectivity of the catalyst, which is defined as the ratio of 2,6-xylenol yield to combined yield of 2,4-xylenol and mesitol, was determined from these average yields. Also measured was off-gas evolution in standard cubic feet per hour (SCFH), which is proportional to the amount of methanol decomposition to carbon monoxide and hydrogen. The results are given in Table I, compared with a control catalyst prepared by a similar procedure but containing 0.5% copper.

TABLE I

|  | Control | Ex. 1 | Ex. 2 | Ex. 3 |
| --- | --- | --- | --- | --- |
| 2,6-Xylenol, % | 52.7 | 73.5 | 72.7 | 71.1 |
| o-Cresol, % | 23.0 | 13.4 | 11.3 | 11.3 |
| p-Cresol, % | 0.10 | 0 | 0.002 | 0.021 |
| 2,4-Xylenol, % | 1.12 | 0.38 | 0.26 | 0.38 |
| Mesitol, % | 9.7 | 8.4 | 11.2 | 12.8 |
| Selectivity | 4.74 | 8.23 | 6.28 | 5.31 |
| Off-gas, SCFH | 0.68 | 0.40 | 0.57 | 0.79 |

As the data in Table I show, the selectivity of the catalysts of this invention is much higher than that of the control. Also, the catalysts of this invention give a substantially higher yield of 2,6-xylenol than the control. Moreover, except in the case of Example 3 the off-gas production of the catalyst of this invention was substantially lower than that of the control.

EXAMPLE 7

Following the procedure of Example 6 except for an LHSV of 2.1, the catalyst of Example 4 was compared with a magnesium oxide catalyst similar to that disclosed in U.S. Pat. No. 3,446,856. The results are given in Table II.

TABLE II

|  | Control | Ex. 4 |
| --- | --- | --- |
| 2,6-Xylenol, % | 68.0 | 73.8 |
| o-Cresol, % | 17.7 | 14.6 |
| p-Cresol, % | 0.02 | 0.09 |
| 2,4-Xylenol, % | 0.20 | 0.20 |
| Mesitol, % | 6.0 | 6.4 |
| Selectivity | 10.96 | 11.18 |
| Off-gas, SCFH | 0.40 | 0.44 |

The results in Table II show that while the selectivity and off-gas production of the copper-containing catalyst of this invention are comparable to those of the control, the yield of 2,6-xylenol is substantially higher.

In addition to the above-described advantages, the catalysts of this invention are characterized by long active life, typically remaining active for 800 hours or more of use.

What is claimed is:

1. A method for preparing a solid catalyst composition which comprises preparing, at a temperature within the range of about 50°–100° C., a slurry of (1) a substantially water-insoluble magnesium reagent which yields magnesium oxide upon calcination in (2) an aqueous solution of at least one copper salt, the copper content of said slurry being about 0.02–0.1% by weight of the magnesium reagent content thereof, thereby producing a magnesium-containing solid phase with a copper-containing coating of submicroscopic thickness thereon; removing and drying said solid phase; and calcining the same at a temperature within the range of about 350°–550° C.

2. A method according to claim 1 wherein the copper content of said slurry is about 0.02–0.04% by weight of the magnesium reagent content thereof.

3. A method according to claim 2 wherein the magnesium reagent is at least one of magnesium oxide, magnesium hydroxide and magnesium carbonate and the slurry contains about 10–25% by weight thereof.

4. A method according to claim 3 wherein the solid phase is formed into pellets after drying and before calcining.

5. A method according to claim 4 wherein the pellets additionally contain at least one filler in an amount up to about 25% by weight, based on copper plus magnesium oxide.

6. A method according to claim 5 wherein the filler is at least one of polyphenylene oxide and graphite in an amount up to about 25% and about 5% by weight, respectively.

7. A method according to claim 5 wherein the magnesium reagent is basic magnesium carbonate.

8. A method according to claim 7 wherein calcination is effected by heating in the presence of hydrogen at about 375°–550° C. before catalyst use.

9. A method according to claim 7 wherein calcination is effected by heating at about 350°–450° C. in contact with an alkylation feed stream comprising at least one alkanol and at least one hydroxyaromatic compound.

10. A method according to claim 8 or 9 wherein the copper salt is cupric nitrate.

11. A catalyst composition prepared by a method according to claim 1, 2, 4, 5 or 6.

12. A catalyst composition comprising magnesium oxide and about 0.02–0.1% by weight, based on said magnesium oxide, of copper, said copper being deposited on said magnesium oxide in elemental or chemically combined form in a layer of submicroscopic thickness.

13. A composition according to claim 12 wherein the copper content is about 0.02–0.04% by weight.

14. A composition according to claim 13 having a surface area of about 50–400 m.$^2$/g.

15. In a method for alkylating at least one hydroxyaromatic compound having a free ortho-position by the catalytic reaction of the same with at least one primary or secondary alkanol containing up to 7 carbon atoms, the improvement which comprises carrying out said reaction at a temperature up to about 475° C. in the presence of a solid catalyst composition prepared by a method which comprises preparing, at a temperature within the range of about 50°–100° C., a slurry of (1) a substantially water-insoluble magnesium reagent which yields magnesium oxide upon calcination of (2) an aqueous solution of at least one copper salt, the copper content of said slurry being about 0.02–0.1% by weight of the magnesium reagent content thereof, thereby producing a magnesium-containing solid phase with a copper-containing coating of submicroscopic thickness thereon; removing and drying said phase; and calcining the same at a temperature within the range of about 350°–500° C.

16. A method according to claim 15 wherein the copper content of said slurry is about 0.02–0.04% by weight of the magnesium reagent content thereof.

17. A method according to claim 16 wherein the alkanol is methanol and the hydroxyaromatic compound is a monohydroxyaromatic compound in which the para-position is unsubstituted.

18. A method according to claim 17 wherein the solid phase is formed into pellets after drying and before calcining, said pellets additionally containing at least one filler selected from the group consisting of polyphenylene oxide and graphite in amounts up to about 25% and about 5% by weight, respectively, based on copper plus magnesium oxide.

19. A method according to claim 18 wherein calcination is effected by heating in the presence of hydrogen at about 375°–550° C. before catalyst use.

20. A method according to claim 19 wherein the hydroxyaromatic compound is phenol or o-cresol.

21. A method according to claim 20 wherein the alkylation temperature is about 420°–450° C.

22. A method according to claim 18 wherein calcination is effected by heating at about 350°–450° C. in contact with an alkylation feed stream comprising at least one alkanol and at least one hydroxyaromatic compound.

23. A method according to claim 22 wherein the hydroxyaromatic compound is phenol or o-cresol.

24. A method according to claim 23 wherein the alkylation temperature is about 420°–450° C.

25. In a method for alkylating at least one hydroxyaromatic compound having a free ortho-position by the catalytic reaction of the same with at least one primary or secondary alkanol containing up to 7 carbon atoms, the improvement which comprises carrying out said reaction at a temperature up to about 475° C. in the presence of a catalyst composition comprising magnesium oxide and about 0.02–0.1% by weight, based on said magnesium oxide, of copper, said copper being deposited on said magnesium oxide in elemental or chemically combined form in a layer of submicroscopic thickness.

26. A method according to claim 25 wherein the alkanol is methanol and the hydroxyaromatic compound is a monohydroxyaromatic compound in which the para-position is unsubstituted.

27. A method according to claim 26 wherein the catalyst composition has a surface area of about 50–400 m.$^2$/g. and a copper content of about 0.02–0.04% by weight.

28. A method according to claim 27 wherein the hydroxyaromatic compound is phenol or o-cresol.

29. A method according to claim 28 wherein the alkylation temperature is about 420°–450° C.

* * * * *